(12) United States Patent
Elmén et al.

(10) Patent No.: US 8,529,503 B2
(45) Date of Patent: Sep. 10, 2013

(54) MEDICAMENT DELIVERY DEVICE

(75) Inventors: Gunnar Elmén, Huddinge (SE); Sebastian Karlsson, Sundbyberg (SE)

(73) Assignee: SHL Group AB, Nacka Strand (SE)

( * ) Notice: Subject to any disclaimer, the term of this patent is extended or adjusted under 35 U.S.C. 154(b) by 70 days.

(21) Appl. No.: 13/265,221

(22) PCT Filed: Apr. 19, 2010

(86) PCT No.: PCT/SE2010/050422
§ 371 (c)(1), (2), (4) Date: Oct. 19, 2011

(87) PCT Pub. No.: WO2010/123439
PCT Pub. Date: Oct. 28, 2010

(65) Prior Publication Data
US 2012/0035538 A1 Feb. 9, 2012

(30) Foreign Application Priority Data
Apr. 24, 2009 (SE) ........................... 0950273

(51) Int. Cl.
*A61M 37/00* (2006.01)

(52) U.S. Cl.
USPC ............ 604/89; 604/187; 604/200; 604/218; 604/220

(58) Field of Classification Search
USPC ............ 604/82–92, 187, 188, 191, 192, 195, 604/200, 201, 202, 206, 207, 218, 220, 232
See application file for complete search history.

(56) References Cited

U.S. PATENT DOCUMENTS
5,769,824 A 6/1998 Hjertman et al.
7,736,333 B2 * 6/2010 Gillespie, III ................. 604/110
8,372,031 B2 * 2/2013 Elmen et al. .................... 604/89

FOREIGN PATENT DOCUMENTS
EP 0834330 A2 4/1998
WO 00/35520 A1 6/2000

OTHER PUBLICATIONS
Swedish Patent Office, Intl Search Report in PCT/SE2010/050422, Jul. 28, 2010.
Swedish Patent Office, Written Opinion in PCT/SE2010/050422, Jul. 28, 2010.

\* cited by examiner

*Primary Examiner* — Theodore Stigell
(74) *Attorney, Agent, or Firm* — Potomac Patent Group PLLC

(57) ABSTRACT

The present invention relates to a medicament delivery device comprising a generally elongated housing comprising a proximal part (10) and a distal part (12); a medicament cartridge (18) comprising a proximal opening closed by a septum (30), an axially movable distal stopper (26), and a first enclosure (20) wherein a liquid and a gaseous fluid are enclosed; a medicament delivery member (36) attachable to said proximal part (10) and having a non-delivery end (34); a medicament cartridge holder (16) wherein the medicament cartridge is coaxially arranged, said cartridge holder being arranged coaxially movable inside said proximal part and comprising holding means (38, 40) capable of holding said medicament cartridge holder (16) in a non-activated position in which said cartridge holder is releasebly engaged to said proximal part and in which a predetermined distance is present between the septum and the non delivery end; a manual pressure mechanism arranged to be moved from a non-pressure position to a pressure position wherein a pressure is build-up inside said cartridge; and an activation mechanism arranged to interact with said holding means only when said manual pressure mechanism is in the pressure position for disengaging said cartridge holder from said non-activated position to an activated position in which said cartridge holder is axially displaced said predetermined distance whereby said septum is penetrated by the non-delivery end and the liquid is expelled due to the pressure built inside the enclosure.

10 Claims, 7 Drawing Sheets

MEDICAMENT DELIVERY DEVICE

TECHNICAL AREA

The present invention relates to a medicament delivery device and in particular a medicament delivery having a low number of components.

TECHNICAL BACKGROUND

It is becoming more and more common to use medicament delivery devices of the injection type wherein the injection sequence in many instances is performed automatically upon activation by the user. In the majority of the medicament delivery devices the injection is performed by a plunger rod acting on a stopper inside a medicament delivery device, where the plunger rod is urged forward by a force means, generally some sort of spring such as a compression spring.

Although the use of injection springs works well in many instances, they have a few drawbacks. One is that they tend to make the device rather long because it has to house the length of the plunger as well as at least a part of the injection spring, even though a part of the spring may be positioned inside the plunger rod. Another drawback is how to handle the force from the injection spring. In some devices, the device is delivered from factory with a pre-tensioned spring. Because there is a risk that the device may be stored for long periods of time before use, the design has to take care of problems with material creeping due to the built-in force, whereby certain components have to be designed with a higher safety factor and/or other types of materials, e.g. metal instead of plastic, which makes the device more expensive. In other devices the device is delivered without the spring being pre-tensioned, and the device is designed such that the tensioning of the spring is performed by the user prior to injection. The drawback here is that the device requires additional components in order for the user to perform the tensioning of the spring.

A few attempts with devices without injection springs have been done. The document WO 00035520 discloses an injector having a reservoir containing compressed gas. When a user presses an activating button a seal is ruptured in the reservoir wherein the compressed gas is led to act on a floating plunger. The plunger in its turn pushes against mated pistons thereby expelling a drug. The drawback with this solution is that it requires a component, the gas reservoir, which is at least as expensive as a spring, which requires quite a lot of space in the device, and also needs to be replaced if the injector is to be used several times. Further, the long time storage may affect the reservoir in many negative ways such that the device may not be functional anymore.

Another aspect of the invention is that it is becoming more and more common to use multi-chamber medicament cartridges in medicament delivery devices such as injectors. The reason for this is that the medicament can be stored for much longer time periods without being degraded in comparison with medicament dissolved in some liquid.

Thus the medicament and the liquid are kept in different compartments in the medicament cartridge and are mixed just before use by moving a dividing wall or stopper such that the compartments can communicate with each other.

However, the multi-chamber medicament cartridges entail more handling steps before a dose of medicament can be injected in that the plunger rod of the injector has to move the stopper of the medicament cartridge in order to initiate the mixing.

A number of solutions have been proposed for obtaining the mixing, from manual operation such as bringing together two parts of the injector to an automatic operation. A manual operation is described in EP 0 288 443 in which a front cover of the injector is rotated whereby a medicament powder chamber is pushed against a plunger, which in turn breaks an aluminium membrane such that liquid is mixed with the powder. This design is rather simple and requires few components, i.e. a robust design and function is obtained.

BRIEF DESCRIPTION OF THE INVENTION

The aim of the present invention is to provide a medicament delivery device that utilizes multi-chamber that is user-friendly and safe when handled, addressing the drawbacks of the state of the art devices.

This aim is obtained by the present invention defined by the features of the independent patent claim. Preferable embodiments of the invention form the subject of the dependent patent claims.

According to a major aspect of the invention, it is characterised by a generally elongated housing comprising a proximal part and a distal part; a medicament cartridge comprising a proximal opening closed by a septum, an axially movable distal stopper, and a first enclosure wherein a liquid and a gaseous fluid are enclosed; a medicament delivery member attachable to said proximal part and having a non-delivery end; a medicament cartridge holder wherein the medicament cartridge is coaxially arranged, said cartridge holder being arranged coaxially movable inside said proximal part and comprising holding means capable of holding said medicament cartridge holder in a non-activated position in which said cartridge holder is releasebly engaged to said proximal part and in which a predetermined distance is present between the septum and the non-delivery end; a manual pressure mechanism arranged to be moved from a non-pressure position to a pressure position wherein a pressure is build-up inside said cartridge; and an activation mechanism arranged to interact with said holding means only when said manual pressure mechanism is in the pressure position for disengaging said cartridge holder from said non-activated position to an activated position in which said cartridge holder is axially displaced said predetermined distance whereby said septum is penetrated by the non-delivery end and the liquid is expelled due to the pressure built inside the enclosure.

There are several advantages with the present invention. A manual operation provides a simple, and yet reliable mixing and/or pressure build-up in the medicament cartridge with few components. This pressure is then used to perform the delivery of the medicament without the use of force/driving means.

A further advantage is the safety regarding unwanted premature delivery since the holding means is kept locked by a safety locking means until the mixing and/or the pressure build-up has been performed.

A further robust and very functional feature is that the activation mechanism comprises a push button that acts directly for firstly activating the device only after mixing and/or the pressure build up, and then acts directly for allowing the medicament cartridge to be connected to the medicament delivery member by the internal pressure, which pressure then causes the delivery of a dose of medicament.

Further in order to facilitate the handling of the device, indicia are arranged and visible in a window on the device, which provides the user with information that the activation mechanism is in a non-pressure position, that mixing has occurred and/or that the activation mechanism is in a pressure position. Apart from visual information, also audible and/or tactile information is provided on the device.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
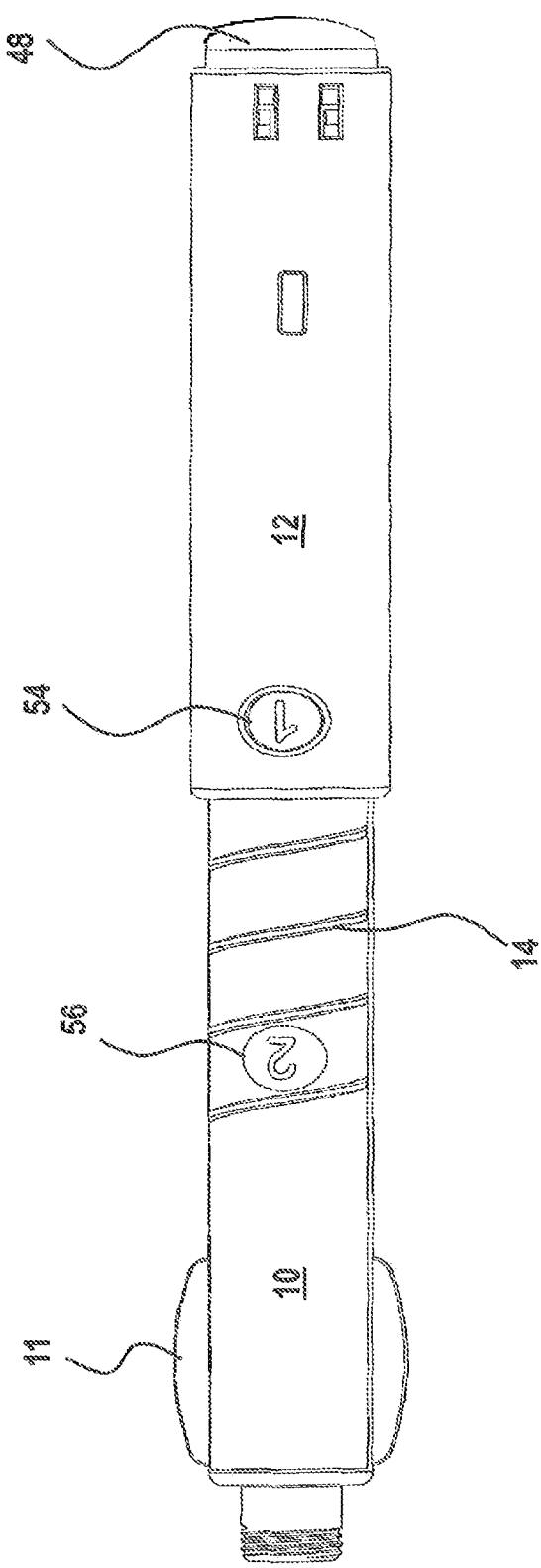
FIG. 1 is a side view of a medicament delivery device according to the present invention in an initial state.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The medicament delivery device comprises:
- a generally elongated housing comprising two housing parts having distal and proximal ends, a proximal part 10 and a distal part 12;
- a medicament cartridge 18 comprising a proximal opening closed by a septum 30, an axially movable distal stopper 26, and a first enclosure 20 wherein a liquid and a gaseous fluid are enclosed;
- a medicament delivery member 36 attachable to said proximal part 10 and having a non-delivery end 34;
- a medicament cartridge holder 16 wherein said medicament cartridge is coaxially arranged, said cartridge holder being arranged coaxially movable inside said proximal part 10 and comprising holding means 38, 40 capable of holding said medicament cartridge holder 16 in a non-activated position in which said cartridge holder is releasebly engaged to said proximal part 10 and in which a predetermined distance is present between the septum 30 and the non-delivery end 34;
- a manual pressure mechanism comprising the housing parts 10, 12 and a static plunger rod 44 which is arranged between said distal stopper 26 and the distal end of said distal part 12; wherein said manual pressure mechanism is arranged to be moved from a non-pressure position in which said housing parts are coaxially and movably connected to each other and said plunger rod is abutting said distal stopper to a pressure position in which said housing parts are inwardly moved in relation to each other such that the plunger rod 44 is moved into the medicament cartridge 18 causing a pressure build-up inside said enclosure; and
- an activation mechanism arranged to interact with said holding means only when said manual pressure mechanism is in the pressure position for disengaging said cartridge holder from said non-activated position to an activated position in which said cartridge holder is axially displaced said predetermined distance whereby said septum is penetrated by the non-delivery end 34 and the liquid is expelled due to the pressure built inside the enclosure.

The two housing parts 10, 12 shown in the drawings are connected to each other via threads 14 but may even be connected by any other kind of engagement means, the function of which will be described below. The medicament cartridge shown in the drawings is of the type of a multi-chamber medicament cartridge 18 but the medicament delivery device may also be used with a one chamber cartridge wherein a liquid medicament and a gaseous fluid are enclosed. The multi-chamber medicament cartridge 18 comprises a first enclosure 20 having a liquid and a gaseous fluid wherein the liquid may be a diluent, a second enclosure 22 having a lyophilized/liquid medicament agent, at least one channel between said first and second enclosure and an axially movable proximal stopper 24 dividing said first and second enclosures. The distal stopper 26 is arranged at the distal end of the cartridge and the cartridge has a proximal neck 28 at its proximal end, wherein the septum 30 is arranged. The septum is made of a resilient pierceable material such as rubber. The proximal neck 28 is positioned in a neck 32 of the proximal end of the proximal housing part 10. The neck 32 of the proximal housing part is arranged with attachment means for attaching the medicament delivery member 36, e.g. a needle, as shown in the drawings. It is however to be understood that different types of medicament delivery members may be used with the present invention, such as nozzles, mouthpieces and the like.

The holding means comprises at least one flexible arm 38 arranged in the distal part of said medicament cartridge holder 16. Each arm is arranged with an outwardly protruding ledge 40 releasebly engaged to a fixed surface 41 on said proximal housing part. The ledges also have an inclined and distally directed surface 42, the function of which will be described below. The static plunger rod 44 comprises a proximal end which is contact with the distal stopper and a distal end which is fixedly connected to a proximal central part 60 of the distal end of the distal housing part 12.

The activation mechanism comprises a push button 48 having proximally directed arms 62 arranged to act on said flexible arms 38 only when said manual pressure mechanism is in the pressure position such that the ledges 40 are moved out of contact from said fixed surfaces 41.

The device further comprises a safety locking means 50 surrounding and axially movable in relation to said plunger rod, and arranged in contact with said arms 38 such that it is moved out of contact with said arms when said manual pressure mechanism is in the pressure position. The safety actuation means 50 shown in the drawings is a ring-shaped member arranged slidable along the plunger rod 44. When the medicament cartridge holder 16 is in the non-activated position, the ring-shaped member is positioned in grooves 52 arranged on the inner surface of the arms 38 such that they are prevented from flexing radially inwards. The distal housing part 12 is further arranged with at least one opening or window 54 on its surface in the proximal part thereof. The proximal housing part 10 is further arranged with at least one indicia means 56 that may be visual and/or audible and/or tactile for providing sufficient information for the user about the status of the device i.e. non-used, mixed medicament, used or the like. As an example of said indicia is at least one resilient tongue with a coloured outwardly extending protrusion that clicks in the at least one window 54 when the manual pressure mechanism is moved from the non-pressure position to the pressure position providing audible, visual and tactile information. Said indicia may also be numbers, which are visible in the window 54 of the distal housing part 12 in a manner that will be described below. The indications 56 visible in the window 54 may be other, like symbols, text, letters and the like capable of providing sufficient information for the user.

The device is intended to function as follows. When the medicament cartridge is a single chamber cartridge and the patient is to take a dose of medicament, the window 54 of the distal housing part displays the number "1" indicating that the activation mechanism is in the non-pressure position. The user then attaches the medicament delivery member, e.g. a needle 36, on the neck portion 32 of the proximal housing part 10, but the non-delivery end 34 of the medicament delivery member 36 does not penetrate the septum 30 of the medicament cartridge 18. As shown in the drawings, the user then threads the proximal housing 10 part into the distal housing part 12, i.e. making the device shorter. This in turn causes the cartridge holder 16 to move in the distal direction into the distal housing part. This relative movement of the cartridge holder 16 and thus medicament cartridge 18 in relation to the plunger rod 44 causes the distal stopper 26 inside to move axially causing a pressure to built up in the gaseous fluid that is present inside the medicament cartridge 18. The turning of the proximal housing part 10 in relation to the distal housing part may be facilitated by at least two grips 11 on the outer surface thereof. When the inwardly displacement of said housing parts in relation to each other is completed, this is indicated by the number "2" in the window 54, which indicates that the activation mechanism is in the pressure position. Also this position could be indicated by a clicking sound and/or a tactile indication.

Figure 2:
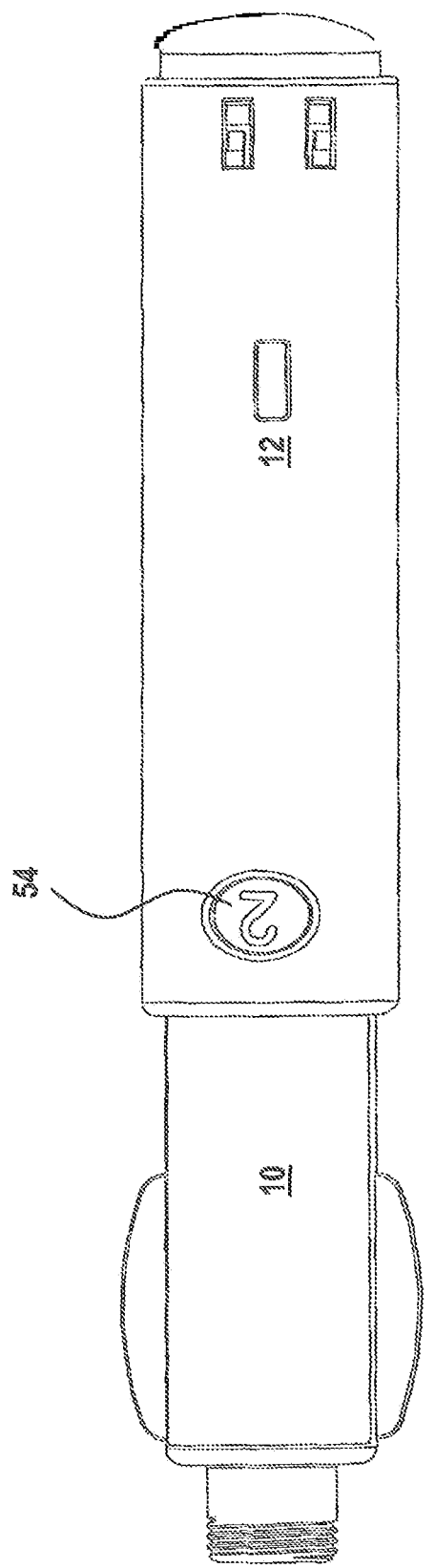
FIG. 2 is a side view of the device of FIG. 1 when a mixing of medicament has been performed.
Figure 3:
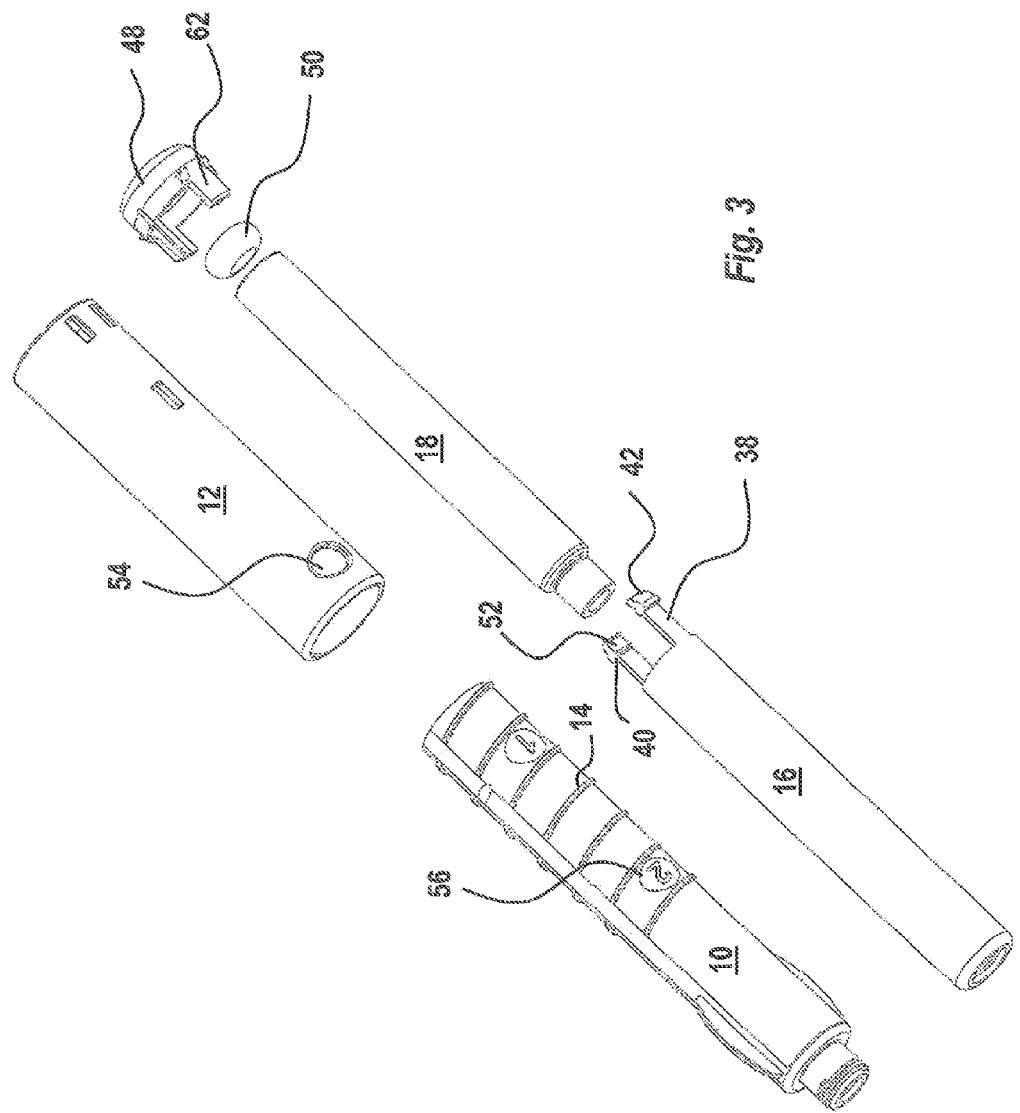
FIG. 3 is an exploded view of the device of FIG. 1.
Figure 4:
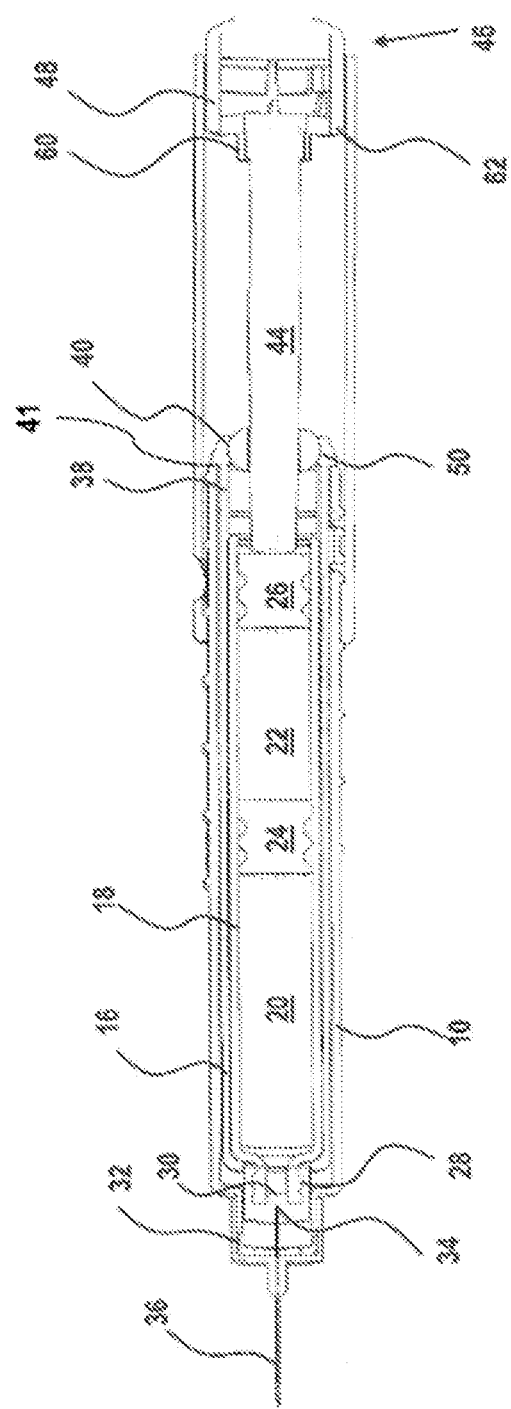
FIG. 4 is a cross-sectional view of the medicament delivery device of FIG. 1 in an initial state.
Figure 5:
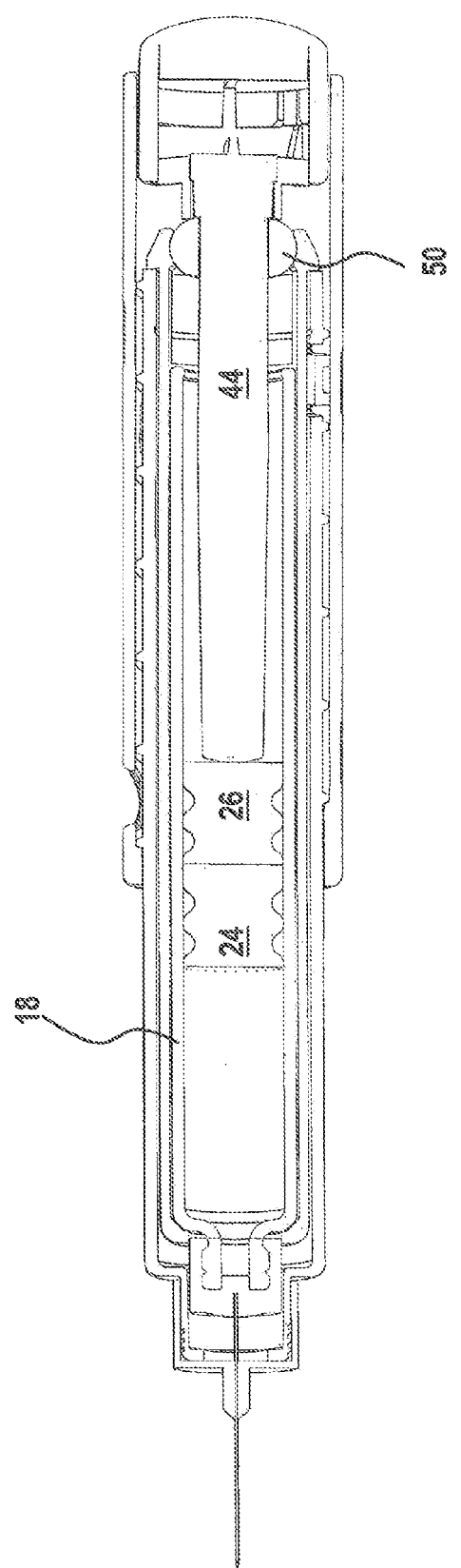
FIG. 5 is a cross-sectional view of the medicament delivery device of FIG. 1 when a mixing has occurred.
Figure 6:
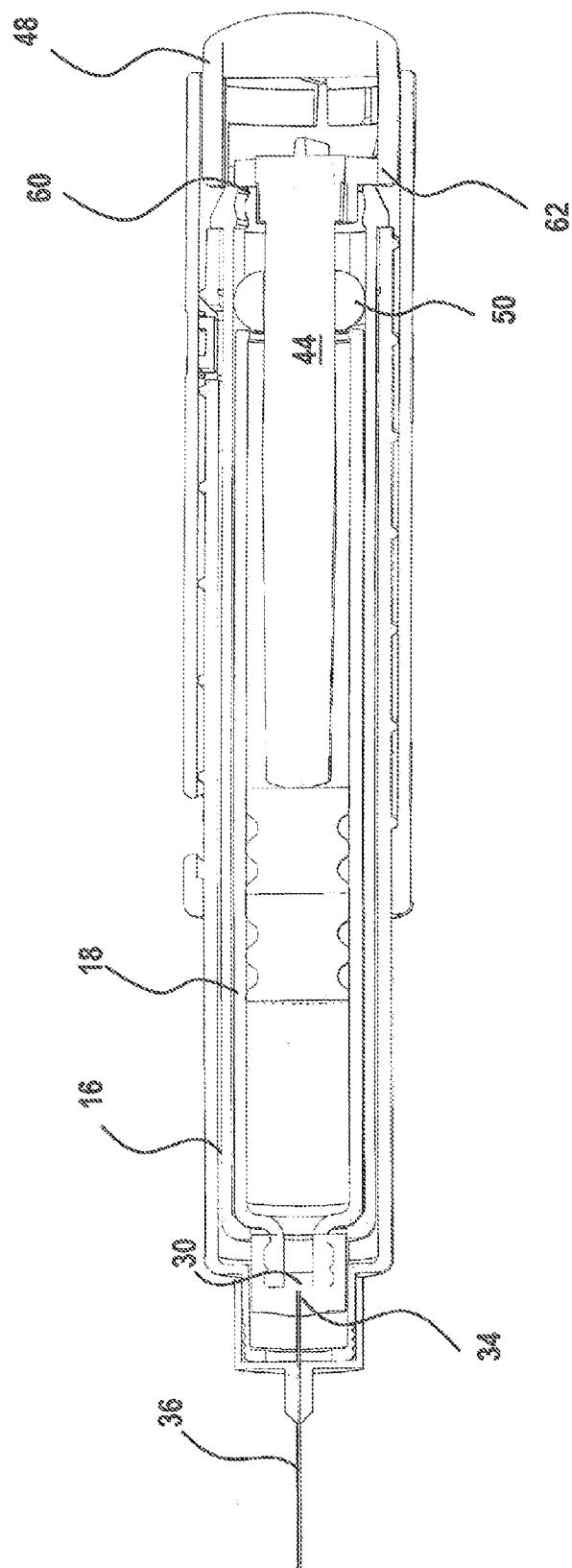
FIG. 6 is a cross-sectional view of the medicament delivery device of FIG. 1 when activated before injection.
Figure 7:
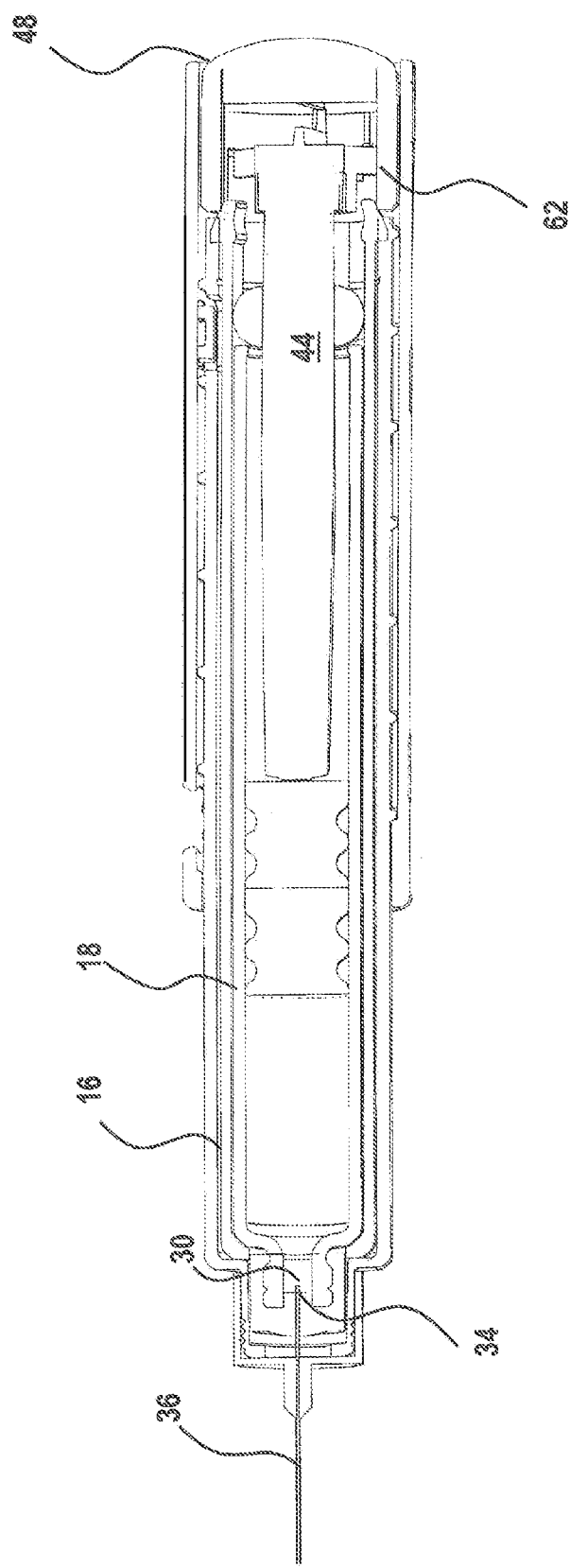
FIG. 7 is a cross-sectional view of the medicament delivery device of FIG. 1 after injection.

Further, when the cartridge is a multiple chamber cartridge and the patient is to take a dose of medicament, the window 54 of the distal housing part displays the number "1" indicating that the activation mechanism is in the non-pressure position, as shown in the drawings, the user then threads the proximal housing 10 part into the distal housing part 12, i.e. making the device shorter. This in turn causes the cartridge holder 16 to move in the distal direction into the distal housing part. This relative movement of the cartridge holder 16 and thus medicament cartridge 18 in relation to the plunger rod 44 causes the distal stopper 26 inside to move axially such that the content in the first enclosure run through the at least one channel into the second enclosure where a mixing of the contents is made, FIGS. 2 and 5. At the same time as the mixing occurs, a pressure is built up in the gaseous fluid that is present inside the medicament cartridge 18. When the mixing is completed, this is indicated by the number "2" in the window 54. Also this position could be indicated by a clicking sound and/or a tactile indication. The user then attaches the medicament delivery member, e.g. a needle 36 as shown in the drawings, on the neck portion 32 of the proximal housing part 10, but the non-delivery end 34 of the medicament delivery member 36 does not penetrate the septum 30 of the medicament cartridge 18. In order to put the activation mechanism in the pressure position, the user turns the two housing parts 10, 12 a further rotational distance, which is indicated by the number "3" in the window 54.

When the activation mechanism is in the pressure position, the distal end of the inclined surfaces 42 of the ledges 40 of the arms 38 abuts against the proximal end of the proximally directed arms 62 of the safety locking means 50 is pushed away by the proximal central part 60, whereby the arms 38 are free to be flexed.

The user now places the delivery device member at the delivery site with the needle 36 and activates the medicament delivery by pressing the push button 48. The distal end of the proximally directed arms 62 of the push button 48 slides on the inclined surfaces 42 of the ledges 40 of the arms 38, whereby the arms flex radially inwards and the ledges 40 are moved out of contact with the distal end surface 41 of the proximal housing part 10. Because of the pressure inside the medicament cartridge 18, the medicament cartridge holder 16 is moved forward whereby the non-delivery end 34 of the medicament delivery member 36 penetrates the septum 30 of the medicament cartridge 18. Due to the pressure inside the medicament cartridge 18, the liquid medicament is pushed through the medicament delivery member 36 and is delivered to the user. When the medicament has been delivered the device can been withdrawn from the delivery site and discarded. Alternatively, the housing parts 10, 12 may be removed from each other and the empty medicament cartridge 18 is replaced by a new medicament cartridge. Then only the medicament delivery member 36 is discarded.

As a further development of the device, the device may also comprise a non-upright locking mechanism (not shown) as at least one titling pendulum or the like connected to said activation mechanism for preventing the activation mechanism to interact with said holding means if the device is not positioned substantially vertical having the delivery member pointing downwards.

It is to be understood that the embodiment described above and shown in the drawings is to be regarded only as a non-limiting example of the invention and that it may be modified in many ways within the scope of the present invention.

The invention claimed is:

1. A medicament delivery device, comprising:
 a generally elongated housing, comprising a proximal part and a distal part, each part having distal and proximal ends;
 a medicament cartridge, comprising a proximal opening closed by a septum, an axially movable distal stopper, and a first enclosure, wherein a liquid and a gaseous fluid are enclosed by the medicament cartridge;
 a medicament delivery member configured for attachment to the proximal part and having a non-delivery end;
 a medicament cartridge holder, wherein the medicament cartridge is coaxially arranged with the medicament cartridge holder, the medicament cartridge holder is arranged coaxially movable inside the proximal part, and the medicament cartridge holder comprises a second holder configured for holding the medicament cartridge holder in a non-activated position in which the medicament cartridge holder is releasably engaged to the proximal part and in which a predetermined distance is present between the septum and the non-delivery end;
 a manual pressure mechanism, comprising the proximal and distal parts and a static plunger rod arranged between the distal stopper and the distal end of the distal part, wherein the manual pressure mechanism is arranged to be moved from a non-pressure position, in which the proximal and distal parts are coaxially and movably connected to each other and the plunger rod abuts the distal stopper, to a pressure position, in which the proximal and distal parts are inwardly moved in relation to each other such that the plunger rod is moved into the medicament cartridge, thereby causing a pressure build-up inside the first enclosure; and
 an activation mechanism arranged to interact with the second holder only when the manual pressure mechanism is in the pressure position for disengaging the medicament cartridge holder from the non-activated position to an activated position, in which the medicament cartridge holder is axially displaced the predetermined distance, whereby the septum is penetrated by the non-delivery end and the liquid is expelled due to the pressure built up inside the first enclosure.

2. The medicament delivery device of claim 1, wherein the medicament cartridge further comprises a second enclosure having a lyophilized/liquid medicament agent, at least one channel between the first and second enclosures, and an axially movable proximal stopper dividing the first and second enclosures.

3. The medicament delivery device of claim 2, wherein contents of the first and second enclosures are mixed when the manual pressure mechanism is moved from the non-pressure position to the pressure position.

4. The medicament delivery device of claim 1, wherein the second holder comprises at least one flexible arm arranged in the distal part of the medicament cartridge holder, and the at least one flexible arm includes a ledge releasably engaged with a fixed surface on the proximal part.

5. The medicament delivery device of claim 4, wherein the activation mechanism comprises a push button arranged to act on the at least one flexible arm such that the ledge is moved out of engagement with the fixed surface.

6. The medicament delivery device of claim 5, wherein the push button is configured for acting on the at least one flexible arm only when the manual pressure mechanism is in the pressure position.

7. The medicament delivery device of claim 4, further comprising a safety locking mechanism surrounding and axially movable in relation to the plunger rod, and arranged in contact with the at least one flexible arm, such that the safety locking mechanism is moved out of contact with the at least one flexible arm when the manual pressure mechanism is in the pressure position.

8. The medicament delivery device of claim 1, wherein the distal part is arranged with a window, and the proximal part is arranged with indicia, such that when the manual pressure mechanism is in a predetermined position, information regarding the predetermined position is displayed by the indicia visible through the window.

9. The medicament delivery device of claim 8, wherein the information comprises at least one of audible information and tactile information.

10. The medicament delivery device of claim 1, further comprising a non-upright locking mechanism connected to the activation mechanism for preventing the activation mechanism from interacting with the second holder when the medicament delivery device is not substantially vertical with the delivery member pointing downward.

* * * * *